US00PP37374P2

(12) United States Plant Patent
Wismans

(10) Patent No.: US PP37,374 P2
(45) Date of Patent: Apr. 21, 2026

(54) ***HELICONIA* PLANT NAMED 'RUBY PARROT IMPROVED'**

(50) Latin Name: *Heliconia psittacorum*
Varietal Denomination: RUBY PARROT IMPROVED

(71) Applicant: Lucanne B.V., Haalderen (NL)

(72) Inventor: Peter Wismans, Haalderen (NL)

(73) Assignee: Lucanne B.V. (NL)

( * ) Notice: Subject to any disclaimer, the term of this patent is extended or adjusted under 35 U.S.C. 154(b) by 0 days.

(21) Appl. No.: 19/289,774

(22) Filed: Aug. 4, 2025

(51) Int. Cl.
*A01H 6/00* (2018.01)
*A01H 5/02* (2018.01)

(52) U.S. Cl.
USPC ..... Plt./263.1

(58) Field of Classification Search
USPC ..... Plt./263.1
See application file for complete search history.

*Primary Examiner* — Karen M Redden

(57) ABSTRACT

A new and distinct cultivar of *Heliconia* plant named 'RUBY PARROT IMPROVED' is disclosed, characterized by solid dark-green foliage color, and bright yellow flower color. Plants are compact and freely-branching. The new variety is a *Heliconia*, typically produced as an outdoor ornamental plant.

2 Drawing Sheets

Latin name of the genus and species: *Heliconia psittacorum.*

Cultivar denomination: 'RUBY PARROT IMPROVED'.

BACKGROUND OF THE INVENTION

The new *Heliconia* cultivar is a product of a whole plant mutation discovered by the inventor at a nursery in Naples Florida. The discovery of this new cultivar took place in June of 2022. The parent variety is *Heliconia psittacorum* 'Ruby Parrot' (not patented).

Asexual reproduction of the new cultivar was performed by tissue culture in January of 2023 at a nursery in De Lier, The Netherlands, and has shown that the unique features of this cultivar are stable and reproduced true to type in successive generations.

SUMMARY OF THE INVENTION

The cultivar 'RUBY PARROT IMPROVED' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'RUBY PARROT IMPROVED' These characteristics in combination distinguish 'RUBY PARROT IMPROVED' as a new and distinct *Heliconia* cultivar:

1. Solid dark green foliage color.
2. Bright flower color.
3. Freely branching with basal branches.
4. Compact growth habit.

Plants of the new cultivar 'RUBY PARROT IMPROVED' are similar to plants of the parent, in most horticultural characteristics, however, plants of the new cultivar 'RUBY PARROT IMPROVED' differ in the following:

1. Plants of the new cultivar are more compact than plants of the parent.

2. Plants of the new cultivar produce more basal branches than plants of the parent.
3. Plants of the new cultivar have a shorter crop time by 14 days than plants of the parent. Crop time is defined by the inventor as the time between planting a tissue culture plantlet until the first flower.

COMMERCIAL COMPARISON

Plants of the new cultivar 'RUBY PARROT IMPROVED' can be compared to the unpatented commercial cultivar *Heliconia* 'Ladi Di Variegated'. These cultivars are similar in most horticultural characteristics, however 'RUBY PARROT IMPROVED' differs in the following:

1. Foliage color of the new cultivar is solid green, while the foliage color of this comparator is variegated.
2. Plants of the new cultivar are more compact than plants of this comparator.

BRIEF DESCRIPTION OF THE PHOTOGRAPHS

Figure 1:
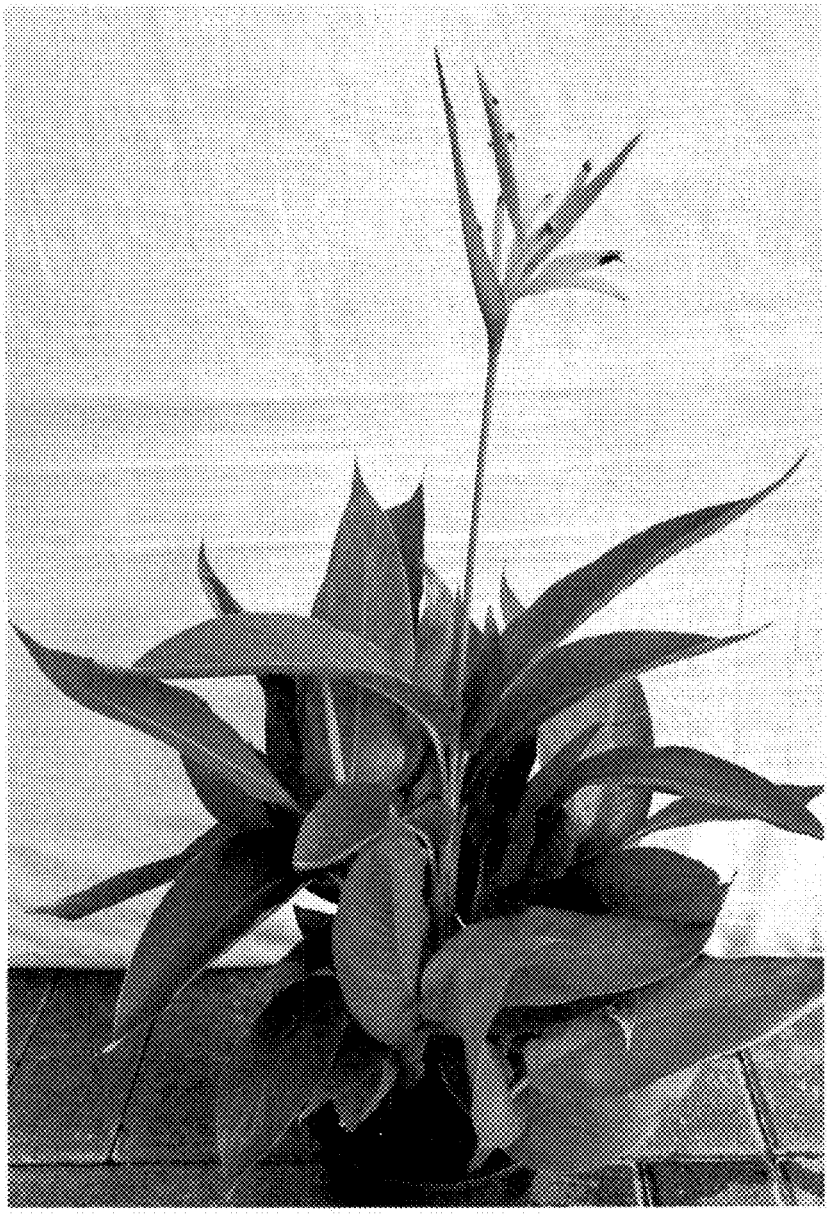

The accompanying photograph in FIG. 1 illustrates in full color a typical plant of 'RUBY PARROT IMPROVED'. Age of the plant photographed is approximately 1.5 years.

Figure 2:
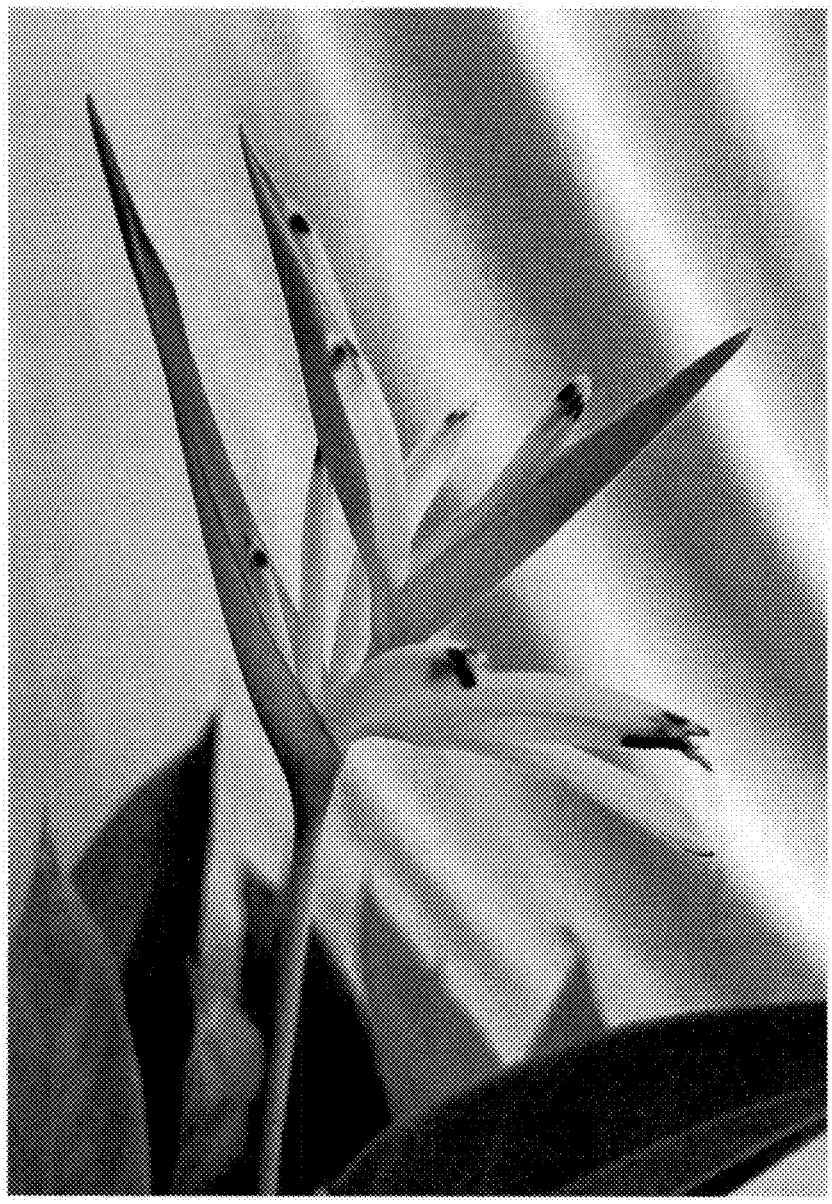

FIG. 2 illustrates a close-up view of a typical flower of the new cultivar.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 1996, except where general terms of ordinary dictionary significance are used. The following observations and measurements describe 'RUBY PARROT IMPROVED' plants grown in a shade house in Key Largo, Florida. The growing temperature ranged from approximately 15° C. to 35° C. during the day and from approximately 15° C. to 20° C. during the night. General light conditions are bright, normal sunlight. Measurements and numerical values represent averages of typical plant types.

Botanical classification: *Heliconia psittacorum* 'RUBY PARROT IMPROVED'.

PROPAGATION

Time to initiate roots: 10 days at approximately 22° C.

Time to produce a rooted cutting: 42 days at approximately 22° C.

Time to produce a finished plant: 100 days at 25° C. from tissue culture.

Rooting habit and description: Clear white, thick roots with fleshy texture.

PLANT

Age of plant described: Approximately 14 weeks.

Growth habit: Upright.

Height: 70 cm to top of floral plane; 38 cm to top of foliar plane.

Spread: 47 cm.

Branching characteristics: Free, basal branching.

Diameter of basal branches: 2.8 cm.

Length of basal branches: 36 cm.

Quantity of basal branches: Approximately 12.

Basal branch strength: Strong.

Stem color: From RHS Yellow-Green 143A flushed Greyed-Red 181A.

Stem shape: Ovate.

Stem pubescence: None.

FOLIAGE

Leaf:
- *Arrangement*.—Alternate, single.
- *Quantity*.—Approximately 6 per stem.
- *Average length*.—25 to 30 cm.
- *Average width*.—6 to 8 cm.

Leaf:
- *Quantity*.—Approximately 5 to 7 per plant.
- *Average length*.—23 to 27 cm.
- *Average width*.—8 to 10 cm.
- *Shape of blade*.—Lanceolate.
- *Apex*.—Apiculate.
- *Base*.—Oblique.
- *Margin*.—Entire.
- *Texture of top surface*.—Glabrous, glossy.
- *Texture of bottom surface*.—Glabrous, glossy.
- *Aspect*.—Reflexed back and folded upward.
- *Color*.—Young foliage upper side: RHS Yellow-Green 144B. Young foliage under side: RHS Yellow-Green 144A. Mature foliage upper side: RHS Green 137B. Mature foliage under side: RHS Green 137C.
- *Venation*.—Type: Pinnate. Venation color upper side: RHS Yellow-Green 144B. Venation color under side: RHS Yellow-Green 144B.

Petiole:
- *Average length*.—4 cm.
- *Average diameter*.—0.4 cm.
- *Color*.—RHS Green 138B.
- *Texture*.—Glabrous, glossy.

INFLORESCENCE

Natural flowering season: Year-round in Florida, US.

Type of inflorescence: Erect cicinnus composed of about 20 true flowers subtended by a showy, boat-shaped bract.

Quantity of inflorescences: About 10 per plant per year.

Quantity of flowers: Average 20 per cicinnus, total 180 per plant per year.

Longevity: 14 days.

Fragrance: None.

Inflorescence size:
- *Height*.—20 cm.
- *Diameter*.—15 cm.

Individual flower:

Flower type: Single.

Flower size:
- *Height*.—11 cm cincinnes height.
- *Diameter*.—9 mm cincinnes diameter.

Pedicel:
- *Length*.—1.5 to 2 mm.
- *Diameter*.—3 mm.
- *Angle*.—20°.
- *Strength*.—Strong.
- *Color*.—RHS Yellow 4A.

Tepals:
- *Number*.—3 per flower.
- *Arrangement*.—Fused into a tube.
- *Length*.—4.5 cm.
- *Width*.—7 mm.
- *Shape*.—Narrow lanceolate.
- *Margin*.—Entire.
- *Apex*.—Acute.
- *Base*.—Oblique.
- *Texture*.—Both sides glabrous.
- *Color*.—Young, upper surface: RHS Yellow 4B. Tip blotched Black 203D. Young, lower surface: RHS Yellow 4C. Tip blotched Black 203D. Mature, upper surface: RHS Yellow 4B. Tip blotched Black 203D. Mature, lower surface: RHS Yellow 4C. Tip blotched Black 203D.

Bud:
- *Shape*.—Narrow lanceolate.
- *Length*.—9 cm.
- *Diameter*.—8 mm.
- *Color*.—RHS Yellow 4A.

Showy subtending bracts:
- *Number*.—3 per flower.
- *Length*.—7 cm.
- *Width*.—7 cm.
- *Shape*.—Boat-shaped.
- *Apex*.—Long acuminate.
- *Color*.—Young, upper surface: RHS Purple-Red 57B. Base streaked Yellow 4B. Young, lower surface: RHS Purple-Red 57C. Base streaked Yellow 4B. Mature, upper surface: RHS Red 57A. Tip flushed Green 139A and Black 203D. Mature, lower surface: RHS Purple-Red 57B. Tip flushed Green 139A and Black 203D.

*Texture*.—Glabrous, shiny, and glossy.
*Margin*.—Entire.

Calyx:
*Length*.—4.5 cm.
*Width*.—7 mm.
*Shape*.—Tubular.

Peduncle:
*Length*.—25 cm.
*Width*.—4 mm.
*Aspect*.—Rigid.
*Angle*.—0°.
*Shape*.—Triangular.
*Texture*.—Smooth.
*Color*.—RHS Yellow-Green 144A.
*Strength*.—Strong.

REPRODUCTIVE ORGANS

Stamens:
*Number*.—*Average* 6.
*Length*.—4.5 cm.
*Width*.—4 mm.

Anthers:
*Shape*.—Linear.
*Length*.—6 mm.
*Width*.—1 mm.
*Color*.—Edge and center RHS Yellow 4B.
*Pollen*.—Not observed.

Pistil:
*Number*.—Approximately 10-15.
*Pistil length*.—Approximately 4 mm.
*Style*.—Length: 5 mm. Color: RHS Yellow 7A.
*Stigma*.—Shape: Three-lobed. Color: RHS Yellow 7A.
*Ovary*.—Length: 3 mm. Color: RHS Yellow 7A.

OTHER CHARACTERISTICS

Seeds and fruits: Not observed.
Disease/pest resistance: Not observed.
Tolerance to weather: Moderate to high.

What is claimed is:

1. A new and distinct cultivar of *Heliconia* plant named 'RUBY PARROT IMPROVED' as herein illustrated and described.

* * * * *